United States Patent [19]

Johnson

[11] 4,356,074
[45] Oct. 26, 1982

[54] SUBSTRATE SPECIFIC GALACTOSE OXIDASE ENZYME ELECTRODES

[75] Inventor: Jay M. Johnson, Dayton, Ohio

[73] Assignee: The Yellow Springs Instrument Company, Inc., Yellow Springs, Ohio

[21] Appl. No.: 181,459

[22] Filed: Aug. 25, 1980

[51] Int. Cl.³ .................. G01N 27/54; C12Q 1/00; C12Q 1/54
[52] U.S. Cl. .................. 204/195 P; 204/1 T; 204/195 B; 435/190; 435/817
[58] Field of Search .............. 204/195 B, 1 E, 195 P; 435/817, 190

[56] References Cited

U.S. PATENT DOCUMENTS

| | | | |
|---|---|---|---|
| 3,919,052 | 11/1975 | Fresnel et al. | 435/817 X |
| 4,016,044 | 4/1977 | Fresnel et al. | 435/817 X |
| 4,073,713 | 2/1978 | Newman | 204/195 B |
| 4,129,478 | 12/1978 | Racine et al. | 204/1 T |
| 4,220,503 | 9/1980 | Johnson | 204/1 T |
| 4,224,125 | 9/1980 | Nakamura et al. | 204/195 B |

OTHER PUBLICATIONS

G. A. Hamilton et al., "Oxidase and Related Redox Systems", 103, (1965).
Paul J. Taylor et al., Anal. Chem., vol. 49, No. 6, pp. 789–794, (1977).

Primary Examiner—G. L. Kaplan
Attorney, Agent, or Firm—Biebel, French & Nauman

[57] ABSTRACT

The relative specificity of the enzyme galactose oxidase for various substrates is controlled as a function of the electrical potential applied to the enzyme. The enzyme is incorporated into a thin layer electrochemical cell laminate having exterior membrane layers and an interior enzyme layer. An electrode located within the enzyme layer applies varying electrical potentials to the enzyme. An intermediate electron transfer agent may be used to transfer electrons to and from the enzyme and electrode.

11 Claims, 7 Drawing Figures

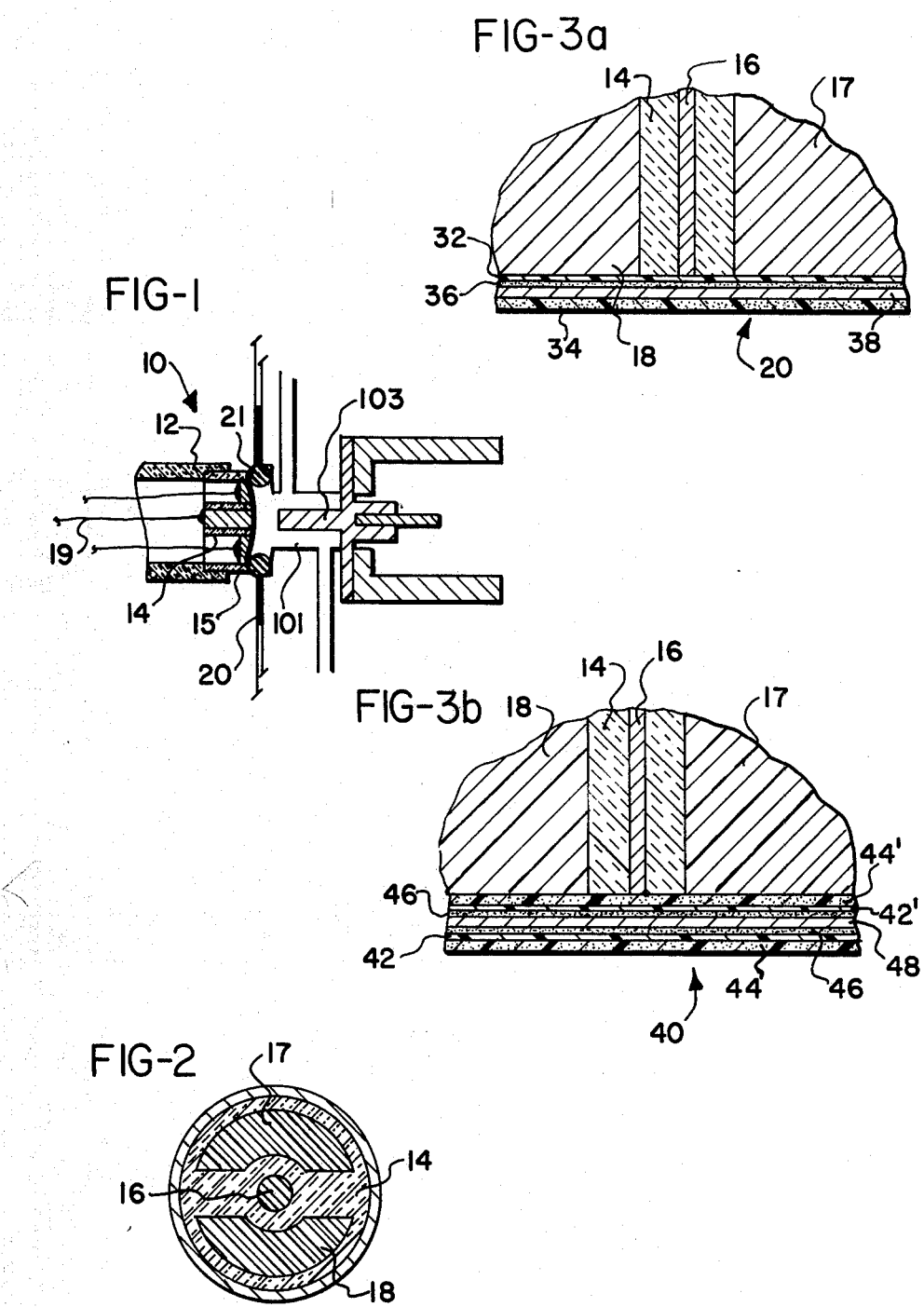

SUBSTRATE SPECIFIC GALACTOSE OXIDASE ENZYME ELECTRODES

BACKGROUND OF THE INVENTION

This invention relates to enzyme electrodes, and in particular to a substrate specific galactose oxidase enzyme electrode utilizing a thin-layer electrochemical cell to control the relative specificity of the enzyme.

Polarographic cell systems have become quite popular in recent years for measurement of various substances. In addition, enzymes have been used in polarographic cells, especially in instances where the unknown substance to be measured is not itself polarographically active, but a material produced or consumed by an enzymatic reaction with that unknown is detectable. For example, it is known that galactose is not polarographically active but that the following reaction takes place in the presence of the enzyme galactose oxidase:

The hydrogen peroxide produced by the reaction can be measured in a polarographic cell such as the system taught by Clark, U.S. Pat. No. 3,539,455. Since the hydrogen peroxide produced is in direct proportion to the amount of galactose present, it is theoretically possible to quatitatively determine the amount of galactose present in a substrate where this is unknown. Likewise, it is possible to quantitatively determine the amount of galactose present by measuring the amount of oxygen used in the above reaction mechanism.

Unfortunately, the enzyme galactose oxidase is a nonspecific enzyme which catalyzes the production of hydrogen peroxide and oxygen consumption from a variety of substrates including galactose, glycerin, dihydroxyacetone, and glyceraldehyde. In many instances, two or more of these compounds will be present together. For example, galactose and glycerin are both found in blood plasma. Present polarographic measuring systems using galactose oxidase are incapable of distinguishing between these compounds because of the nonspecificity of galactose oxidase. Accordingly, the need exists in the art for a method of controlling the relative substrate preference of galactose oxidase in order to enable determinative polarographic measurements to be made.

It is known that certain enzymes and other proteins show an activity dependence based upon the reduction-oxidation (redox) potentials of solutions containing such enzymes. For example, Santhanam et al, 99 *J. American Chemical Society*, 274 (1977), reported that the enzyme urease when adsorbed onto the surface of a mercury coated thermistor, reversibly lost activity (as measured by a temperature change on the thermistor) at a given reducing potential. However, this technique has only limited utility for those proteins which will adsorb directly onto mercury, has a slow response time, and is not very sensitive.

Hamilton et al, 1 *Oxidases and Related Redox Systems*, 103 (1965), in theory teach "control" of the potential of a solution which also contained the enzyme galactose oxidase. Hamilton and his coworkers used a given ratio of ferricyanide to ferrocyanide to chemically control the solution potential. Then, by adding galactose and monitoring the uptake of oxygen with a Clark oxygen electrode to determine activity, they plotted the activity dependence on the solution potential (ratio of ferri-to-ferrocyanide). This approach was time consuming since several solutions had to be made up but, also another problem with it was the uncertainty in the true solution potential seen by the enzyme. The results from the fact that the ratio of ferricyanide to ferrocyanide is not controlled after these compounds are added to the solution and obviously this ratio can change both before and/or during the determination of activity.

Finally, Heineman et al, 47 *Anal. Chem.* 79 (1975), calculated the formal oxidation-reduction potentials ($E^0$) for several enzymes using a thin layer electrochemical cell. By applying a series of differing potentials to a solution containing the enzyme of interest, the ratio of oxidized to reduced components was measured spectrophotometrically and used to plot a linear graph, the intercept of which yielded a formal redox potential value ($E^0$).

Likewise, Caja in "Thin-Layer Cell for Routine Applications," 61 *Analytical Chemistry*, 1328 (July 1979), describes a thin layer cell and a wire thin layer electrode. The thin layer electrode was surrounded by Nafion cation exhcange tubing. These workers stressed the permselectivity of the cation exchange membrane and the resulting benefit that only small amounts of solutions containing electroactive anions and/or electroactive large neutral species were required for electrochemical studies. No provisions were made for the introduction of substrates under controlled conditions into the thin layer cell. Also, the configuration described would preclude the rapid determination of enzymatic activity due to the slow equilibration of substrate across the thick Nafion membrane.

Thus, to my knowledge no one has utilized the control of a redox potential of a solution containing galactose oxidase to control the relative specificity of that enzyme for various substrates in a polarographic system.

Control of enzyme reaction rates in areas other than polarography has been suggested. Fresnel in U.S. Pat. Nos. 4,016,044 and 3,919,052 does so in the field of manufacture and treatment of food products by enzyme catalysis. Fresnel teaches that control of the enzymatic reactions is achieved by applying a potential to an enzymatic electrode (an enzyme fixed on a solid electronically conductive support) and controlling the value of this potential during the reaction so as to compensate for variations in the reaction conditions and the enzyme activity and thereby ensure a constant reaction rate. In the '052 Patent Fresnel even suggests that the technique "may allow the specificity of . . . [the] enzyme to be modified, if need be." However, there is nothing disclosed in this patent concerning specificity beyond that broad suggestion. Certainly, there is no teaching of control of solution potential in galactose oxidase in order to control the relative specificity of that enzyme for various substrates in a polarographic system.

Accordingly, the need still remains for a method of controlling the relative substrate preference of a nonspecific enzyme such as galactose oxidase in order to enable determinative analytical measurements to be made.

SUMMARY OF THE INVENTION

In accordance with the present invention, the relative specificity of the enzyme galactose oxidase for various substrate materials to be determined polarographically is controlled as a function of a redox potential applied to the enzyme. It is believed that the redox potential control is effective in galactose oxidase because of the presence of copper ion. Galactose oxidase contains a single copper ion. The enzyme is inactive in the reduced state, $Cu^{+1}$, and active in the oxidized state, $Cu^{+2}$ or $Cu^{+3}$. Whatever the reduction/oxidation mechanism, it is possible with this invention to control enzymatic activity electrochemically. In a preferred embodiment of the invention, enzymatic activity is controlled by placing the enzyme in a thin layer electrochemical cell.

The thin layer cell is a laminate having a permeable, outer membrane to separate the electrode from the external bulk solution containing the sample to be analyzed. The thin layer cell itself is less than 10 microns thick and contains the entrapped enzyme which can either be free or immobilized. The electrode may be either a thin grid of electrically conductive material in the thin layer cell or a layer of electrically conductive material sputtered or otherwise deposited on the back side of the permeable membrane separating the bulk solution and enzyme in the thin layer cell.

The back wall of the thin layer cell can be either an impermeable support material or a permeable or semipermeable membrane. Intermediate electron transfer agents (mediators) are preferably present in the thin layer cell for transferring electrons between the enzyme and electrode. The mediators enable rapid achievement of solution potential control in the thin layer cell.

The permeability of the outer membrane separating the thin layer cell from the bulk solution is such that the enzyme cannot pass outwardly through the membrane yet substrates of interest can diffuse into the interior of the thin layer cell. The pore size of the outer membrane is also small enough that electrochemical mediating agents are essentially entrapped within the thin layer cell.

In an alternative embodiment, however, the pores may be large enough to permit rapid diffusion of mediators into and out of the thin layer cell, but cross-linking of the enzyme is therefore desirable. In this embodiment the thin layer cell is not "seen" by the mediator as an electrochemical "thin layer" because the mediator can move freely into and out of the thin layer cell through the membrane. However, because the cell containing the enzyme and electrode is so thin, mediated potential control of the enzymatic redox state can still be maintained. One of the advantages of using this embodiment is that substrates of interest which are larger (over 200 molecular weight) can still diffuse into the thin layer cell. This would not be possible if the mediator had to be completely contained within the thin layer.

In operation, the thin layer cell may be coupled to a polarographic cell having an $H_2O_2$ electrode or to a polarographic cell having an oxygen electrode. The electrode within the thin layer cell is coupled to a source capable of providing varying electrical potential. After standardization, a sample containing one or more substrates of interest is brought into contact with the cell and a series of differing potentials are applied to the electrode within the thin layer cell. By polarographically measuring the relative amounts of hydrogen peroxide produced at each potential or the oxygen uptake (depending on the type of cell used), it is possible to identify the specific substrate or substrates in the sample; although, the preferred major use is in terms of quantitative determination. Thus, a single potential corresponding to a maximum enzymatic activity level for a specific substrate can be applied to the electrode within the thin layer cell and the galactose oxidase enzyme in the thin layer will be used to quantitatively measure the specific substrate of interest.

If there are two or more substrates present and the activity potential dependence is not different enough, then a measurement at each of two potentials (for maximum relative difference) is required for accurate quantitative determination.

Accordingly, it is an object of the present invention to provide a process and apparatus for controlling the relative specificity of an enzyme for various substrate materials in a polarographic system. This and other objects and advantages of the invention will be apparent from the following description, the accompanying drawings, and the appended claims.

BRIEF DESCRIPTION OF THE DRAWINGS

FIG. 1 is a schematic view of a polarographic cell having in place the thin layer electrochemical cell of the present invention;

FIG. 2 is a front view of the face of the electrode arrangement found in FIG. 1.

FIG. 3a is an enlarged view of the lower central portion of the polarographic cell of FIG. 1 and showing in more detail one embodiment of the thin layer electrochemical cell of the present invention; and FIG. 3b is an enlarged view of the lower central portion of the polarographic cell of FIG. 1 and showing in detail a second embodiment of the thin layer electrochemical cell.

DESCRIPTION OF THE PREFERRED EMBODIMENTS

Figure 4A:
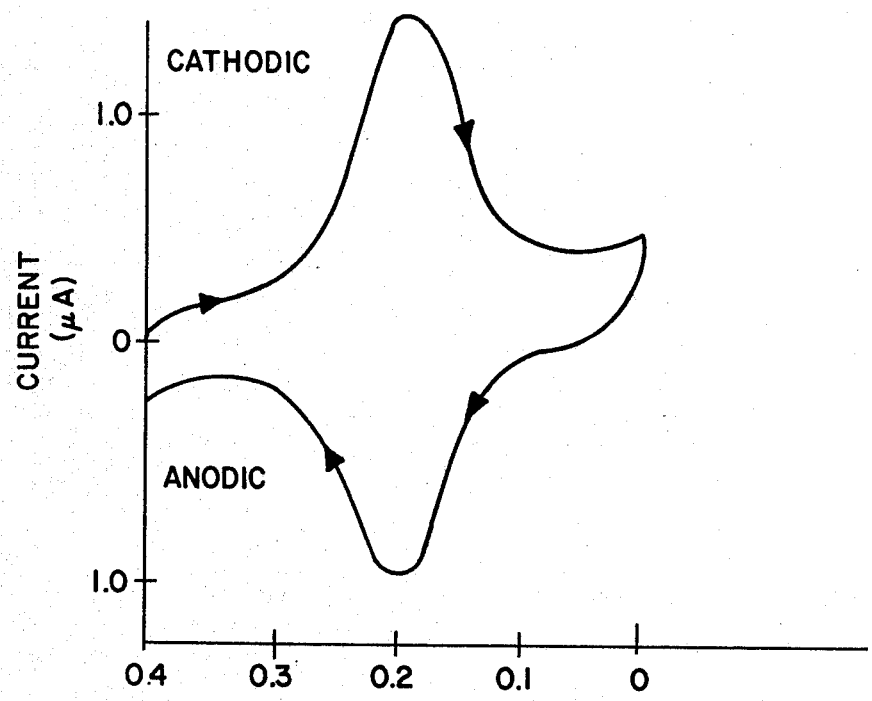
FIG. 4a is the current-potential curve for the oxidation/reduction of ferrocyanide/ferricyanide at the electrode in the thin layer.

Referring to FIG. 1, there is shown a thin layer electrochemical cell of the present invention in combination with a polarographic cell system. The polarographic cell assembly 10 includes an insulating support body 12 of plastic or glass which is preferably cylindrical in shape. Positioned within the cylindrical support body 12 is an electrically insulating member 14 of plastic or glass which supports a platinum anode 16 and two silver/silver chloride electrodes 17 and 18 (see FIG. 2). A conductor 19 is attached to electrode 16.

The lower end of support body 12 is provided with an annular ring or retainer 15, and a thin layer electrochemical cell 20 made in accordance with the present invention is maintained on the end of the support body 12 nearest electrodes 16, 17 and 18. The thin layer cell is held in position on the support body by an O-ring 21 or the like.

In the embodiment illustrated in FIG. 3a, thin layer cell 20 has as a back wall an inner membrane layer 32 against the face of anode 16 and electrodes 17 and 18.

Outer membrane layer 34 will be in contact with the sample to be analyzed. On the back side of outer membrane layer 34, an electrically conductive layer 38 such as gold is deposited by a sputtering or other known process. Electrically conductive layer 38 is used to vary the electrical potential of the enzyme in enzyme layer 36 which in turn varies the relative substrate preference for the enzyme. The enzyme is immobilized in enzyme layer 36 by the addition of binders or cross-linking agents such as glutaraldehyde. A preferred method of forming enzyme layer 36 is to mix the enzyme and binder or cross-linking agent with enough liquid to form a flowable paste which can then be pressed into a thin, uniform layer. Sufficient enzyme must be incorporated into the mixture to provide an adequate reactive amount for measurement.

In the embodiment illustrated in FIG. 3b thin layer cell 40 comprises a pair of coupled membrane layers, outer one 42-44 and inner one 42'-44' sandwiching an enzyme layer 46 which contains an electrode 48 running therethrough. Electrode 48 may comprise a grid of fine gold wire or other electrically conductive material. In this embodiment, the enzyme does not need to be immobilized since the pore size of the membrane layers 42 and 42' is such that the enzyme is too large to pass through.

In both embodiments 3a and 3b, membrane layers 32 and 42, 42' comprises a thin film of essentially homogenous silicone, polymethyl methacrylate, or cellulose acetate. In a preferred embodiment, layers 32 and 42, 42' are an approximately 0.10-1.0 micron thick layer of cellulose acetate having a pore size of 6A° in diameter. Membrane layers 34 and 44, 44' are preferably a 5-10 micron thick polycarbonate film. The pores size may vary. In embodiment 2a membrane 34 has a pore size preferably around 0.03 micron and the pore density of preferably $3 \times 10^8$ pores/cm$^2$. In embodiment 2b the membrane layers 44, 44' are simply gross support layers which may have a pore size of around 12 microns in diameter and a pore density of $1 \times 10^5$ pores/cm$^2$. Membrane layers 44, 44' of FIG. 2b are used as a support for the thinner membrane layers 42, 42' and also acts as a gross filter to screen out very large interfering compounds from the bulk solution to be sampled. A more detailed description of the methods of preparing laminates of membrane layers of this type as well as the preparation of the enzyme layer is found in Newman, U.S. Pat. No. 3,979,274, the disclosure of which is hereby incorporated by reference.

Because of the thinness of the layers, thin layer cell 20 or 40 permits rapid diffusion of the substrate of interest into the cell and exhibits an extremely rapid response time with steady state being reached in less than one minute. In the embodiment shown in FIG. 2a, inner membrane layer 32 is preferably 0.1-1 micron thick, and outer membrane layer 34 is 5-10 microns thick, enzyme layer 36 is around 0.1-2 microns thick, and the electrically conductive layer 38 may be extremely thin so long as the resistance is less than around 1000 ohms/cm$^2$. The embodiment shown in FIG. 3b is only somewhat thicker with membrane layers 42,42' preferably again being 0.1-1 micron thick, membrane layers 44, 44' are 5-10 microns thick, and the overall thickness of the enzyme layer 46 and electrode 48 being about 3-10 microns thick, with the electrode 48 around 1-5 microns.

Referring again to FIG. 1, in operation cell assembly 10 with thin layer cell 20 of the type shown in FIG. 3a, for example, in position is in contact with a sample solution injected into chamber 101 which is stirred by stirring finger 103. In a matter of seconds, oxygen and the substrate of interest will diffuse into the thin layer cell through outer membrane layer 34 and react with the galactose oxidase enzyme in enzyme layer 36. This reaction produces hydrogen peroxide which diffuses through inner membrane layer 32 to contact the active surface of the platinum anode 16. An ammeter (not shown) then measures the amount of hydrogen peroxide produced as a measure of the concentration of the substrate in the sample solution. Because of the extreme thinness of cell 20, there is a delay from the time of hydrogen peroxide production to detection at anode 16 of only a few seconds. A silver/silver chloride electrode 17 acts as a reference electrode and completes the hydrogen peroxide detection circuit.

In cases where there are two or more substrates in the sample solution which will react with galactose oxidase, the relative specificity of the enzyme for a given substrate is controlled by controlling the electrical potential of electrically conductive layer 38 in the thin layer cell 20 which in turn controls the oxidation state of the enzyme in enzyme layer 36. In a preferred embodiment of the invention, an intermediate electron transfer agent (mediator) is present in the enzyme layer 36 and acts to transfer electrons from the electrically conductive layer to the enzyme. An example of such a mediator is potassium ferricyanide which is capable of reversibly exchanging electrons with the electrically conductive layer and enzyme as it is alternately reduced to the ferrocyanide state and reoxidized to ferricyanide. Other suitable mediators may be used such as Co (terpyridine)$_2$Cl$_2$, K$_4$W(CN)$_8$, or 2,6 dichlorophenolindophenol.

In the thin layer cell 40 illustrated in FIG. 3b, the permeability of the coupled inner membrane layers 42'-44', and coupled outer membrane layer 42-44, is such that the enzyme and mediator are essentially entrapped within the cell. However, in the thin layer cell illustrated in FIG. 3a, the pore sizes in outer membrane layer 34 are large enough to permit the rapid passage of mediators into and out of cell 20. In this case, the thin layer cell 20 is no longer a "thin layer" in the electrochemical sense to the mediator since it is free to diffuse into and out of the cell. Yet, mediated potential control of the oxidation and reduction states of the enzyme can be maintained because of the thinness of the membrane layers. This is an advantage in cases where a substrate of interest is large and could not be introduced into the thin layer cell if it were necessary to completely contain the mediator in the cell.

Electrical potentials are applied to electrically conductive layer 38 (FIG. 3a) and electrode 48 (FIG. 3b) by a potentiostat of conventional operational amplifier design. A silver/silver chloride electrode 18 acts as a reference electrode for the potential control circuit while a platinum electrode (not shown) may be placed in the sample solution to act as an auxiliary electrode.

The invention may be better understood by reference to the following nonlimiting examples.

EXAMPLE

A thin layer cell as shown in FIG. 3b was constructed using a gold grid electrode and galactose oxidase as the enzyme. A scanning rate of 2 millivolts/second was used. The substrate tested for was glycerin. The enzyme layer contained buffered $4 \times 10^{-3}$ molar potassium ferricyanide as a mediator. The sample solution had a pH of 7.3 and also contained $4\times10^{-3}$ molar potassium ferricyanide in 0.5 molar potassium chloride with a 0.07 molar phosphate buffer. As shown by the cyclic voltammogram in FIG. 4A, which is a current-potential curve for the oxidation/reduction of ferrocyanide/ferricyanide ion at the gold grid, as the potential of the gold grid is scanned from 0 volt versus Ag/AgCl to 0.4 volt, the anodic current peak indicates the oxidation of ferrocyanide ion to ferricyanide. A reversal of the scan results is a cathodic peak due to the reduction back to ferrocyanide. Since the mediator is trapped within the cell, the voltammogram exhibits a typical thin layer behavior with negligible peak separation and peak widths at a half-height of approximately 90 millivolts.

Figure 4B:
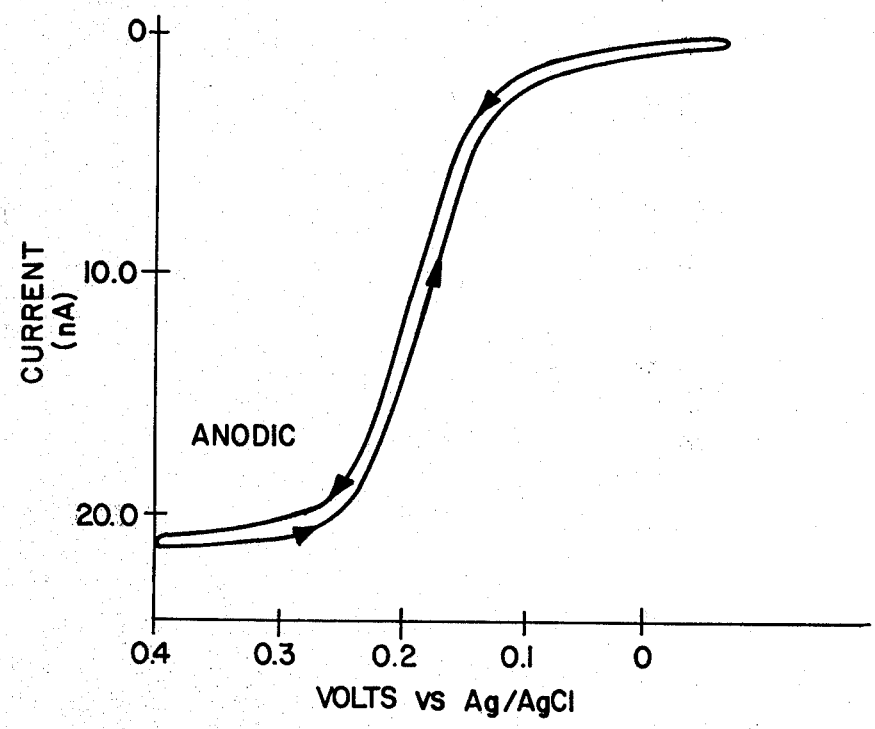
FIG. 4b is an activity potential profile for the galactose oxidase catalyzed oxidation of glycerin having a plot of the hydrogen peroxide current resulting from the enzyme reaction.

A positive potential scan converts the galactose oxidase into its oxidized form which catalyzes the substrate's reaction with oxygen. The reaction produces hydrogen peroxide which is detected by the platinum electrode. FIG. 4B is a plot of the hydrogen peroxide current measured amperometrically as the gold grid electrode was scanned at 2 millivolts/second. Scanning began after the glycerin substrate was introduced into the stirred sample solution until a final concentration of about $5\times10^{-3}$ molar and a steady state hydrogen peroxide current had been achieved. The onset of a limiting current at about 0.3 volt versus Ag/AgCl is indicative of complete galactose oxidase conversion to its oxidized form. The approximate reversibility of the oxidation/reduction reaction is indicated by the reverse scan behavior shown in FIG. 4B.

The voltammogram of FIG. 4B is a unique measurement of enzyme activity as a function of solution potential. The shape of the wave is determined by several factors including diffusion of the substrate from the sample solution into the thin layer, the fraction of galactose oxidase which is in the enzymatically active oxidation state, the kinetics of the substrate enzyme reaction, and subsequent diffusion of hydrogen peroxide to the platinum electrode. Results utilizing other substrates indicate that the wave shape will differ for different substrates.

Figure 5:
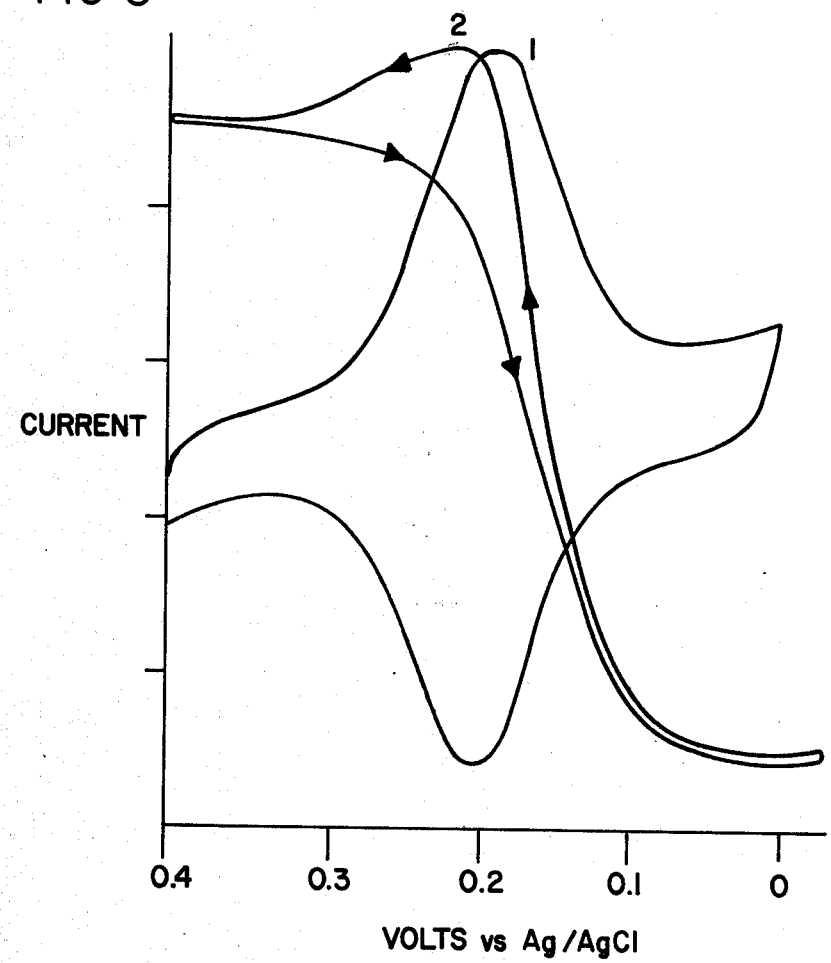
FIG. 5 is an activity potential profile for the galactose oxidase catalyzed oxidation of dihydroxyacetose, showing both the current-potential curve for the oxidation/reduction of ferrocyanide/ferricyanide (1) and a plot of the hydrogen peroxide current (2) resulting from the enzyme reaction.

For example, FIG. 5 shows a plot of the hydrogen peroxide current measured amperometrically as a function of the potential of the gold grid when a dihydroxyacetone substrate was introduced into a sample solution at a final concentration of about $3\times10^{-4}$ molar. Superimposed over it is the current-potential curve for the oxidation/reduction of ferrocyanide/ferrocyanide similar to that depicted in FIG. 4A. A comparison of FIGS. 4A, 4B and 5 shows that by controlling the potential of the gold grid, and with it the oxidation state of galactose oxidase, the relative specificity of the enzyme for various substrates can be controlled. By measuring the relative amounts of hydrogen peroxide produced as the potential of the gold grid is changed, the specific substrates which react with galactose oxidase may be identified and their relative concentrations determined by polarographic measurement.

In this manner an enzyme electrode may be used to determine those substrates for which galactose oxidase will catalyze the production of hydrogen peroxide. It can do so rapidly and accurately with specificity as to the particular substrate involved.

While the process and apparatus herein described constitute preferred embodiments of the invention, it is to be understood that the invention is not limited to this precise process and apparatus, and that changes may be made therein without departing from the scope of the invention.

What is claimed is:

1. A thin layer electrochemical cell capable of controlling the relative specificity of an enzyme for various substrates for use in rapid, direct analytical analysis of those substrates comprising:
   a first outer membrane layer adapted to be adjacent a substrate solution for allowing passage of low molecular weight materials into said cell but excluding high molecular weight materials contained in said substrate solution,
   second inner membrane layer adapted to be adjacent to a polarographic cell for excluding passage of interfering low molecular weight materials and any mediator but permitting the passage of the electroactive reactant or product of the reaction between said substrate or substrates and an enzyme,
   an enzyme preparation positioned between said first and second membrane layers, said enzyme being one which is subject to redox potential control, and
   an electrically conductive layer between said first and second membrane layers and contacting said enzyme preparation, said electrically conductive layer connected to a potential control means capable of varying the electrical potential of said enzyme preparation,
   said cell being thin and capable of use in rapid, direct analytical analysis of said substrates.

2. The electrochemical cell of claim 1 in which said enzyme preparation contains galactose oxidase.

3. The electrochemical cell of claim 2 in which said first membrane layer is a polycarbonate film.

4. The electrochemical cell of claim 3 in which said second membrane layer is an essentially homogeneous material selected from the group consisting of silicone rubber, methyl methacrylate, and cellulose acetate.

5. The electrochemical cell of claim 4 in which said electrically conductive layer means comprises a layer of gold deposited on the back wall of said first membrane means.

6. The electrochemical cell of claim 2 in which said enzyme preparation additionally contains an intermediate electron transfer agent.

7. The electrochemical cell of claim 2 in which said first membrane layer comprises a coupled membrane layer of a first polymeric material which acts as a support for a second polymeric material, said second polymeric material having a plurality of pores the diameter of which is less than the diameter of the pores in said first polymeric material.

8. The electrochemical cell of claim 7 in which said second membrane layer comprises a coupled membrane layer of a first polymeric material which acts as a support for a second polymeric material, said second polymeric material having a plurality of pores the diameter of which is less than the diameter of the pores in said first polymeric material.

9. The electrochemical cell of claim 1 in which said electrically conductive layer means comprises a grid of gold wires.

10. In a polarographic cell structure for use in polarographic analysis of a substrate in a substrate solution comprising a polarographic electrode means mounted with said polarographic cell structure, said polarographic electrode means including means defining an active exposed working face, the improvement comprising:

a thin layer electrochemical cell separating said polarographic electrode means from said substrate solution, said thin layer electrochemical cell having, a first outer membrane layer adapted to be adjacent the substrate solution for allowing passage of low molecular weight materials into said cell but excluding high molecular weight materials contained in said substrate solution, second inner membrane layer adapted to be adjacent to a polarographic cell for excluding passage of interfering low molecular weight materials but permitting the passage of the electroactive reactant or product of the reaction between said substrate(s) and an enzyme, an enzyme preparation positioned between said first and second membrane layers, said enzyme being one which is subject to redox potential control, and an electrically conductive layer between said first and second membrane layers and contacting said enzyme preparation, said electrically conductive layer connected to a potential control means capable of varying the electrical potential of said enzyme preparation, said thin layer electrochemical cell rendering said polarographic cell structure capable of rapid, direct analytical analysis for said substrate.

11. The polarographic cell structure of claim 10 wherein said enzyme preparation contains galactose oxidase.

* * * * *